United States Patent [19]

Masanobu

[11] Patent Number: 4,672,650
[45] Date of Patent: Jun. 9, 1987

[54] TOMOGRAPHIC TESTING APPARATUS

[75] Inventor: Kazunori Masanobu, Tokyo, Japan

[73] Assignee: Kabushiki Kaisha Toshiba, Kawasaki, Japan

[21] Appl. No.: 699,089

[22] Filed: Feb. 7, 1985

[30] Foreign Application Priority Data

Feb. 16, 1984 [JP] Japan .................................. 59-27436
Feb. 16, 1984 [JP] Japan .................................. 59-27437

[51] Int. Cl.⁴ .............................................. A61B 6/02
[52] U.S. Cl. ........................................... 378/4; 378/99; 378/901; 358/111
[58] Field of Search ................. 378/20, 21, 4, 99, 901; 358/111

[56] References Cited

U.S. PATENT DOCUMENTS

| | | | |
|---|---|---|---|
| 4,149,247 | 4/1979 | Pavkovich et al. | 378/901 |
| 4,225,789 | 9/1980 | Albrecht | 378/901 |
| 4,349,739 | 9/1982 | Annis | 358/111 |
| 4,415,980 | 11/1983 | Buchanan | 378/21 |
| 4,481,651 | 11/1984 | Haendle | 378/22 |

FOREIGN PATENT DOCUMENTS 0130891 10/1979 Japan .................................. 378/901

Primary Examiner—Craig E. Church
Assistant Examiner—David P. Porta
Attorney, Agent, or Firm—Oblon, Fisher, Spivak, McClelland & Maier

[57] ABSTRACT

The tomographic testing apparatus employs two data collection modes. One of these modes is a reference data collection mode in which almost all of the prescribed image data of a reference sample is obtained. The reference sample has no defect. The other of these modes is a measurement mode in which a predetermined small number of image data of an inspection sample is obtained. The inspection sample to be tested may have defective portions. The tomographic image of the inspection sample is obtained from the combination of the inspection sample image data and the reference sample image data from which specific data corresponding to the inspection sample image data is deleted.

17 Claims, 29 Drawing Figures

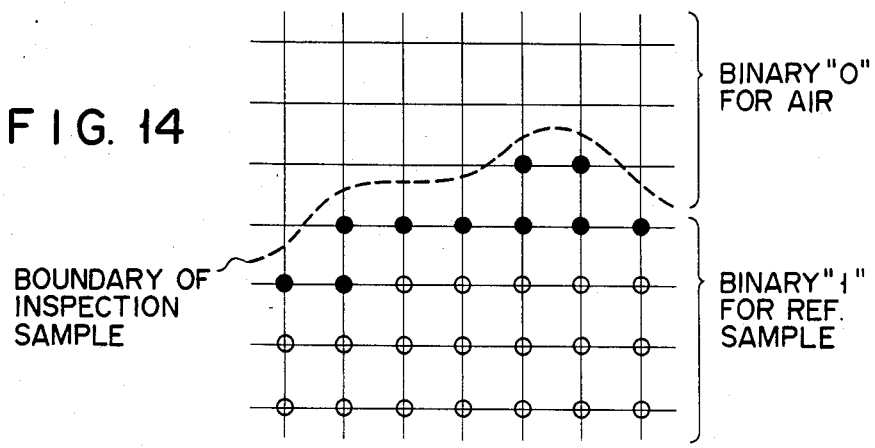
F I G. 14
BINARY "0" FOR AIR
BOUNDARY OF INSPECTION SAMPLE
BINARY "1" FOR REF. SAMPLE
F I G. 15A
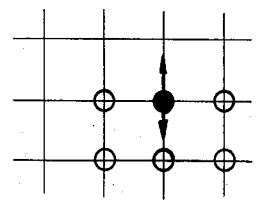
F I G. 15B
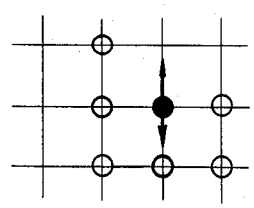
F I G. 15C
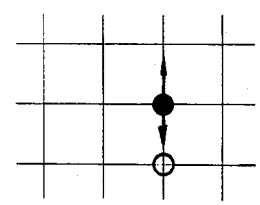
F I G. 15D
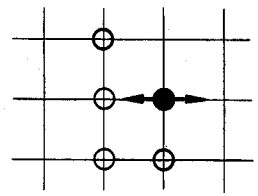
F I G. 15E
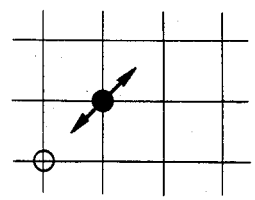
F I G. 15F
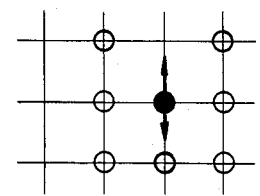
F I G. 15G
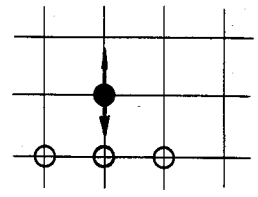
F I G. 15H
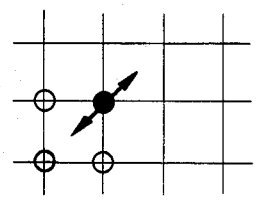
F I G. 15I
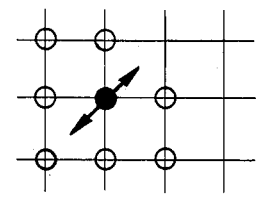

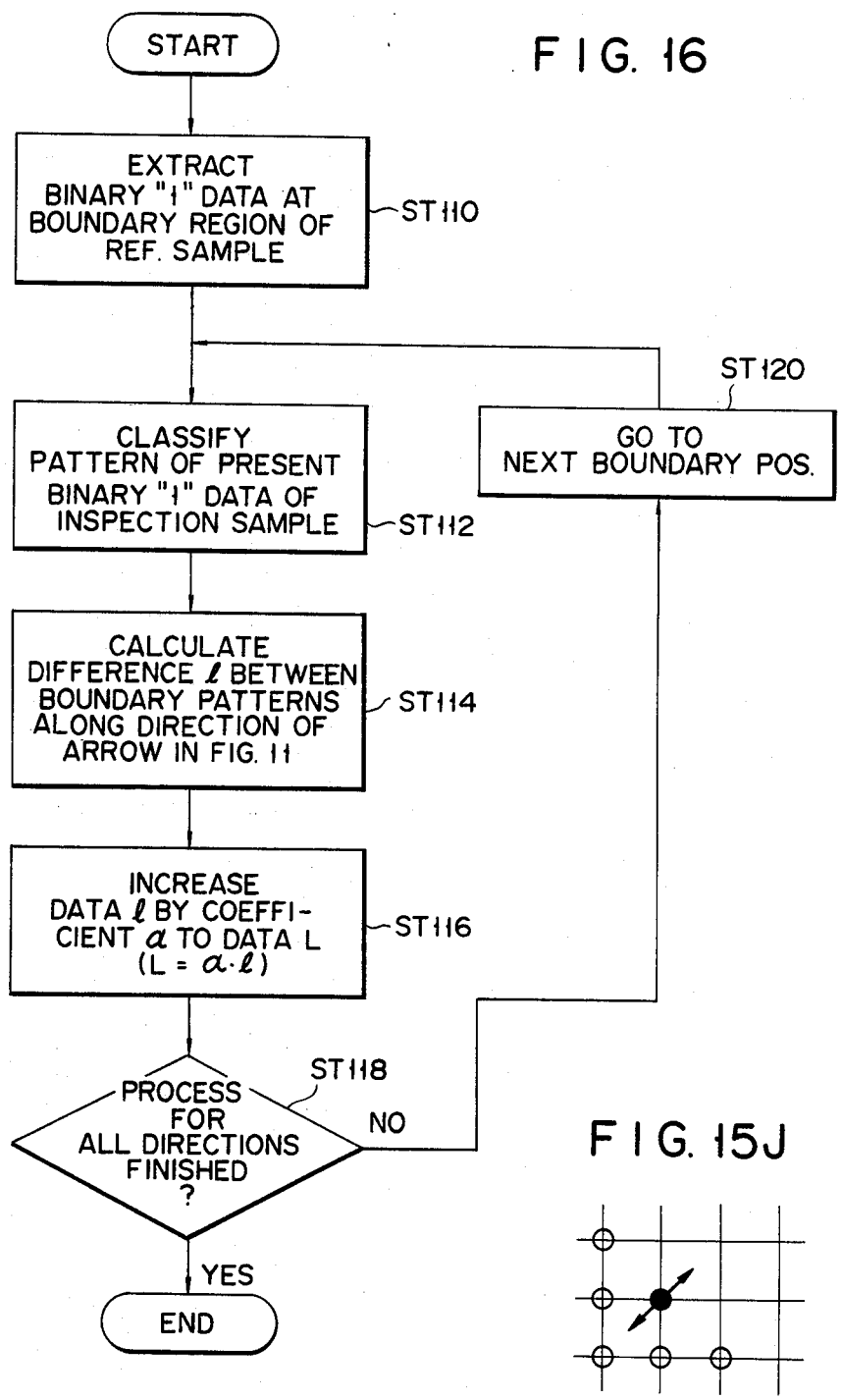

TOMOGRAPHIC TESTING APPARATUS

BACKGROUND OF THE INVENTION

The present invention relates to tomographic (or sectional radiographic) equipment being adapted to inspect and/or analyze defects in a given object, particularly relating to X-ray or γ-ray tomographic testing apparatus for nondestructive testing of size, dimensions and/or inner defects in industrial products.

Tomographic equipment called as a "computerized tomography scanner (CT scanner)" may be utilized to safely and accurately inspect the inner defects, tissues, construction, etc. of materials. Such a CT scanner is provided with a radiation source and radiation detector. The radiation source generates a fan beam X-ray which is spreaded along a two-dimensional sector plane. The radiation detector is opposed to the radiation source with a slice of an object to be inspected therebetween. The detector is formed with a plurality of radiation sensors which are arranged around the radial directions of the spreaded X-ray sector plane. When the source-detector configuration is rotated 360 degrees around the object in a steps of one degree, a large amount of data representing X-ray absorption of the object slice for respective angles of 360 degrees is obtained.

A tomographic image corresponding to the obtained X-ray absorption data is reconstructed by means of computer processing. The reconstructed tomographic image of respective portions in the inspected object slice may have a thousand gradations, and therefore, a precise inspection or analysis of the object material can be achieved.

In recent years, it has been proposed that a CT scanner be applied to nondestructive testing of size, dimensions and/or inner defects of industrial products. Such a CT scanner may have a configuration as shown in FIG. 1. (A similar configuration is disclosed in FIG. 1 of U.S. Pat. No. 4,293,912 issued on Oct. 6, 1981).

According to the configuration of FIG. 1, a main body 1 of the scanner has an X-ray source 2. Source 2 radiates a fan beam X-ray FB for each projection within a given spreading range. A radiation detector 3 is opposed to X-ray source 2. Detector 3 includes a large number of tiny radiation sensors which are arranged around the radial directions of the spreaded X-ray sector plane. Each of the radiation sensors senses, with a certain spatial resolution, the intensity of X-ray from source 2. The radiation path defined between source 2 and each of the radiation sensors is called an X-ray path. Each of the radiation sensors delivers an individual signal which indicates the intensity of an X-ray on the corresponding X-ray path.

Scanner main body 1 is provided with a rotation actuator (not shown). X-ray source 2 containing an X-ray tube is mounted on the rotation actuator so that the rotation center of the actuator coincides with the center of a tomography region. The actuator serves to effect a single-way rotary scanning of the X-ray. The rotary scanning angle is sequentially changed by prescribed degrees. An object material 4 to be inspected is placed within the tomography region. An X-ray radiation control, a current and voltage control for the X-ray tube, etc. are performed by an X-ray controller 5. A rotation control for the rotation actuator is achieved by a scanner controller 6. The operation of controllers 5 and 6 is governed by a system controller 7. System controller 7 also governs the whole operation of the CT scanner. Various instructions and/or data required by the system controller 7 are obtained from a console 8. An operator of the scanner may input specific data or instructions to controller 7 through a manipulation of console 8.

Respective outputs E3 (analog) from the radiation sensors of detector 3 are supplied to a data collector 9. Collector 9 includes an A/D converter. According to a control command I7 from system controller 7, the A/D converter converts the analog outputs E3 into digital X-ray absorption data D9 for each projection. Absorption data D9 is supplied to a preprocessor 10. Under the control of system controller 7, data D9 is variously processed through a log-converter, gain corrector, off-set corrector and so on contained in preprocessor 10.

Processed data D10 from preprocessor 10 is convoluted by a convolver 11 upon receipt of command I7 from system controller 7. Convoluted data D11 from convolver 11 is supplied to a back projector 12. In back projector 12, data D11 is back-projected along the projection direction, and reconstruction of a tomographic image of the back-projected data is achieved. Reconstructed image data D12 of the back projection is stored in an image memory (RAM) 13. Data D13 read-out from memory 13 is supplied to an image converter 14. In converter 14, data of a desired range of CT values contained in data D13 (or data being defined in accordance with the degree of X-ray absorption) is image-converted, so that data D14 representing the desired CT range is displayed with various white levels in a monochrome display screen of a CRT display 15.

The CT scanner of FIG. 1 will operate as follows. First, in order to obtain a tomographic image of object 4, an operator of the scanner manipulates the key board of console 8 so that the CT scanner starts to operate. Then, system controller 7 instructs the scanner controller 6 to perform the step rotation of the rotation actuator with a given angle. System controller 7 also instructs the X-ray controller 5 to perform an intermittent application of a given voltage and current to the X-ray tube for each of the step rotations. The period of intermittent voltage and current applications to the X-ray tube for each step rotation is prefixed. By the intermittent application of voltage and current to the X-ray tube, X-ray source 2 sequentially generates pulsate fan beam X-rays FB.

Object 4 is located at the rotation center (tomography region) of the rotation actuator, and X-ray source 2 faces the detector 3 through the rotation center. Accordingly, as the rotation actuator rotates, a specific slice of object 4 is subjected to the radiation of fan beam X-rays FB from various directions. Then, X-ray transmittances of respective X-ray paths for each fan beam X-ray FB are sensed by the radiation sensors of detector 3, and information of the sensed transmittances is converted to outputs E3.

The data regarding the converted outputs E3 is collected by data collector 9. For each of tomographic projections, data collector 9 supplies the collected data D9 to preprocessor 10, so that the collected data D9 is log-converted, gain-corrected, off-set-corrected, etc. Preprocessed data D10 from preprocessor 10, which indicates X-ray absorption of respective X-ray paths for each projection, is convoluted in convolver 11. Convoluted data D11 from convolver 11 is supplied to back projector 12 in which a back-projecting operation is effected. Then, CT values for the locations of respective pixels of an image are obtained, and a tomographic image corresponding to the obtained CT values is reconstructed.

The reconstructed tomographic image is stored in memory 13. In accordance with specific instructions from console 8, the gradation of the CT values regarding a desired region of the stored tomographic image is determined by image converter 14, and the tomographic image with the determined gradation is displayed at CRT display 15. Thus, the reconstructed tomographic image is displayed on the monochrome display screen with given various white levels.

Generally speaking, according to the CT scanner as shown in FIG. 1, about 300 to 600 sets of projection data are needed for an accurate inspection or analysis of industrial products. Namely, tomographic measuring is performed 300 to 600 times for each one rotation of the rotation actuator in scanner main body 1. From this, a long scanning time (5 to 10 seconds or more) is required for each inspection.

Even where the CT scanner of FIG. 1 is used for a relatively simple inspection of industrial products (e.g., a test for merely judging whether or not the inspected product is good), at least a hundred sets of projection data will be required. Accordingly, if such a CT scanner is used for inspecting the inner defects of products to be mass-produced, a smooth, fast flow of mass-produced products in the factory is unobtainable because of the length of time needed for inspection. This is one of the problems to be solved.

Further, in a medical X-ray CT scanner, a reference material is often used for a comparable measurement. In such a comparable measurement, in a preceding step, projection data for a water fantom (reference sample) is obtained for various projection directions. An error due to the characteristic of the CT scanner is detected from the projection data of the water fantom, and values for compensating the error are calculated. Next, in a measuring step, each of inspection materials is set at the tomography region in place of the water fantom, and the obtained projection data for each inspection material is compensated in accordance with the calculated error-compensating values. Then, the compensated projection data is convoluted and back-projected to obtain a reconstructed tomographic image of the inspection material (inspection sample).

Although the above reconstructed tomographic image actually indicates the sectional view of the inspection sample, it is not evident directly from this tomographic image which portion of the inspection sample deviates from the corresponding portion of the reference sample, or it is not evident directly from this tomographic image whether or not the inspected sample is a good one. This is another problem to be solved.

SUMMARY OF THE INVENTION

It is accordingly a main object of the present invention to provide a tomographic testing apparatus having an enhanced testing speed.

An auxiliary object of the invention is to provide a tomographic testing apparatus in which how a tested inspection sample deviates from a reference sample can be gauged from a tomographic image of the inspection sample.

To achieve the main object, a tomographic testing apparatus of the invention employs two data collection modes. One of these modes is a reference data collection mode in which a large number of prescribed image data (e.g., X1, X2, X4, X5, X7, X8 and X10) of a reference sample is obtained. The reference sample has no defect. The other of these modes is a measurement mode in which a predetermined small number of image data (e.g., Y3, Y6 and Y9) of an inspection sample is obtained. The inspection sample may have defective portions. The tomographic image of the inspection sample is obtained from the combination (X1, X2, Y3, X4, X5, Y6, X7, X8, Y9 and X10) of the inspection sample image data (Y3, Y6 and Y9) and the reference sample image data (X1, X2, X4, X5, X7, X8 and X10) from which specific data (X3, X6 and X9) corresponding to the inspection sample image data (Y3, Y6 and Y9) is deleted.

According to the above tomographic testing apparatus, the number of data (Y3, Y6 and Y9) to be actually measured is far less than all data (Y1 to Y10) of the inspection sample. From this, the testing speed of the apparatus is effectively enhanced.

To achieve the auxiliary object, the tomographic testing apparatus of the invention detects reference projection data for a reference sample and inspection projection data for an inspection sample. The difference between the reference projection data and the inspection projection data is reconstructed to obtain a tomographic image of the inspection sample.

According to the above testing apparatus, when the tomographic image of the difference is characterized by color or by any other suitable means, how the tested inspection sample deviates from the reference sample can be seen from the tomographic image.

BRIEF DESCRIPTION OF THE DRAWINGS

FIG. 14 shows a distribution of binary-coded "1" data around the boundary of a reference sample;

FIGS. 15A to 15J respectively illustrate the pattern classify directions along which binary-coded data around the boundary "1" data of an inspection sample is changed from "0" to "1", so that the character of the tested inspection sample is exaggerated;

FIG. 16 is a flow chart explaining how emphasizing or exaggerating of the differece between a reference sample and a tested inspection sample is achieved;

DETAILED DESCRIPTION OF THE PREFERRED EMBODIMENTS

Figure 1:
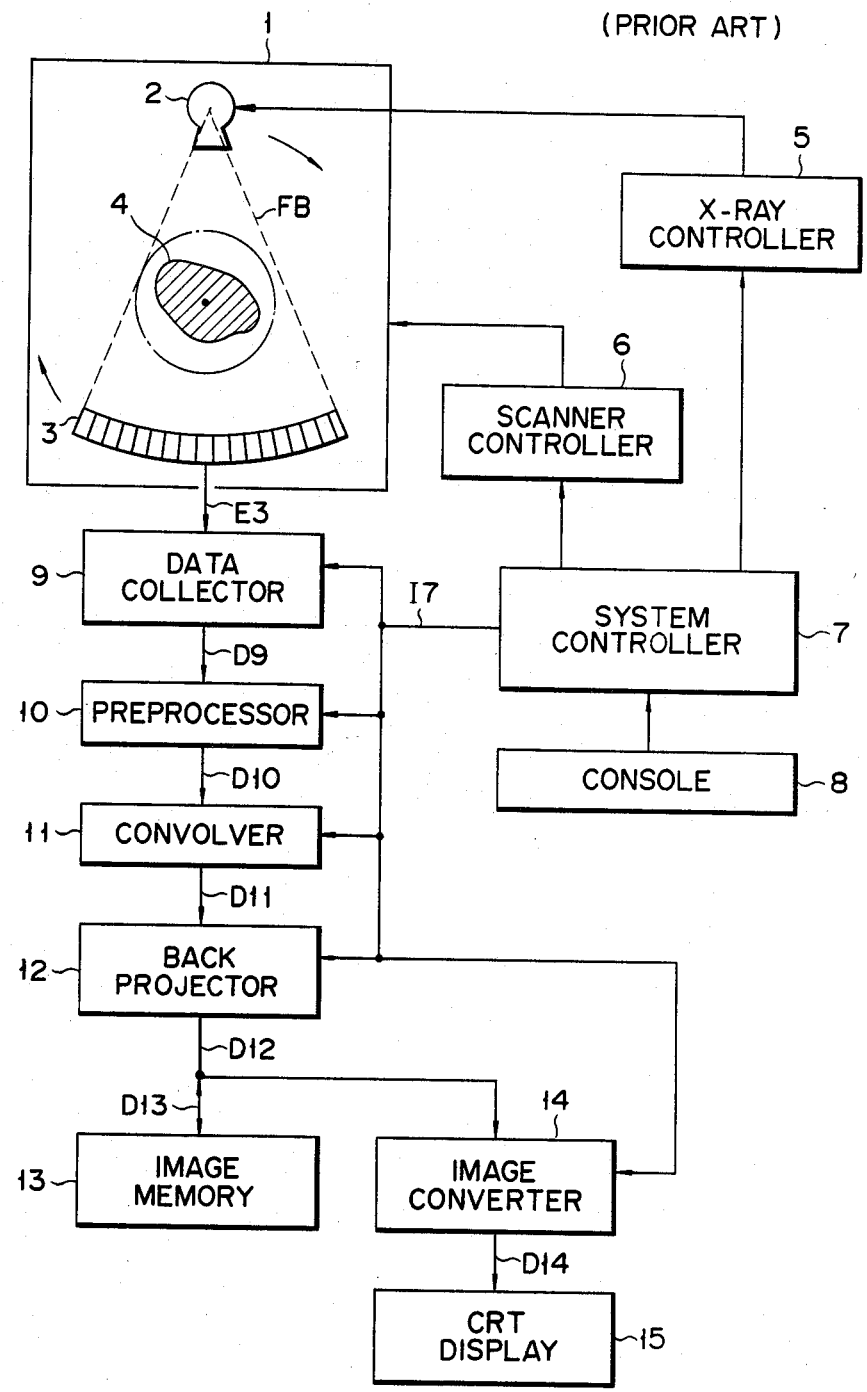
FIG. 1 shows a typical configuration of a conventional X-ray tomographic testing apparatus.

Hereinafter, preferred embodiments of the invention will be described in detail with reference to the accompanying drawings. In the following description, the same elements are denoted by the same reference numerals throughout the drawings, thereby avoiding redundant explanations.

Figure 2A:
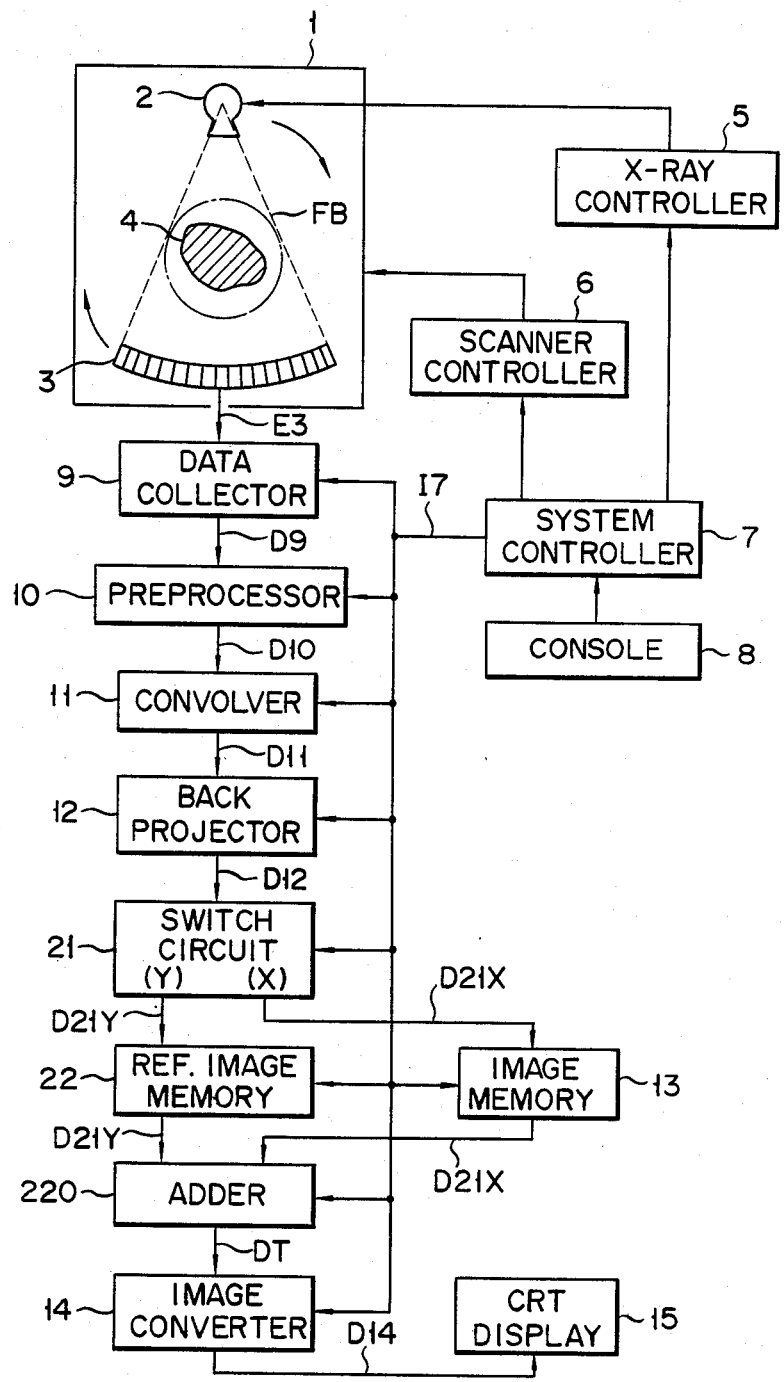
FIG. 2A shows a configuration of an X-ray tomographic testing apparatus according to an embodiment of the present invention.

FIG. 2A is a block diagram showing an X-ray tomographic testing apparatus according to an embodiment of the present invention. In FIG. 2A, elements 1 to 15 may have the same configurations as the corresponding elements in FIG. 1. The key point of this embodiment is that a means (22) for storing information of a reference sample is provided between data collector 9 and image converter 14. In the FIG. 2A embodiment, a switch circuit 21 and reference image memory 22 used as the above storing means are located after the back projector 12. The switching operation of circuit 21 as well as the write/read operation of memories 13 and 22 are controlled by system controller 7.

The tomographic testing apparatus shown in FIG. 2A employs two operation modes. They are a reference data collection mode and a measurement mode. Which of these modes is selected is determined by an operator's manipulation for console 8.

Now, assume that 600 projections are assigned to obtain the tomographic image data for one rotation (360 degrees) around the object. In this case, the pair of X-ray source 2 and radiation detector 3 (source-detector configuration) is rotated around object 4 with 0.6 degree-step, and reconstructed image data D12 of the object 4 can be obtained from back projector 12 for each of the 600 projections.

In the reference data collection mode, switch circuit 21 provides data D21Y corresponding to data D12 in accordance with a command I7 from system controller 7. In this case, all reconstructed image data of a non-defective reference sample for one rotation (i.e., the reconstructed image data of 1st to 600th projections) are stored in reference image memory 22. Or, a prescribed major portion of reconstructed image data (e.g., the reconstructed image data of 2nd to 200th projections, 202nd to 400th projections and 402nd to 600th projections) is stored in reference image memory 22. (In this case, the back projecting operations for 1st, 201st and 401st projections may be deleted.) The prescribed major portion of reconstructed image data stored in memory 22 (2nd to 200th projections, 202nd to 400th projections and 402nd to 600th projections) can be optionally read out. The address of memory 22 for the prescribed major portion of reference sample image data is defined by command I7.

In the measurement mode, in accordance with command I7, switch circuit 21 provides data D21X corresponding to reconstructed image data D12. In this case, a prescribed minor portion of reconstructed image data of a defective inspection sample (e.g., the reconstructed image data of 1st projection, 201st projection and 401st projection) is stored in image memory 13. The address of the prescribed minor portion of inspection sample image data is defined by command I7. When three projections (1st, 201st, 401st) are used in the measurement mode, the angular deviation among these projections is preferably 120 degrees. If four projections (1st, 151st, 301st, 451st) are used in the measurement mode, the angular deviation among these projections is preferably 90 degrees.

Tomographic image data DT of the inspection sample (1st, 2nd–200th, 201st, 202nd–400th, 401st, and 402nd–600th projections) is obtained by combining the prescribed major portion (2nd–200th, 202nd–400th and 402nd–600th) of the reference sample image data from memory 22 with the prescribed minor portion (1st, 201st and 401st) of the inspection sample image data in memory 13. The above combining operation is effected by an adder 220 in such a manner that respective pixels of the reference sample data (D21Y) correspond to those of the inspection sample data (D21X). In the combining operation for the reconstructed image data, the address for each memory 13, 22 is defined by command I7 from system controller 7, so that specific data (1st, 201st and 401st) corresponding to the inspection sample image data is deleted from the reference sample image data (1st–600th). The combined tomographic image data DT is supplied to CRT display 15 via image converter 14.

Figure 3:
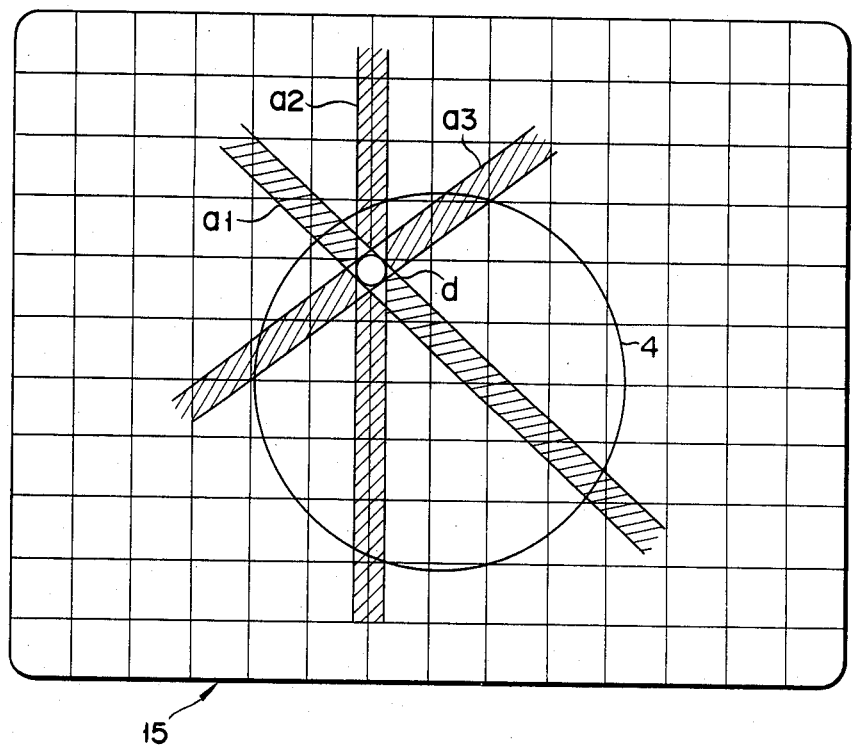
FIG. 3 shows a simplified example of a tomographic image with artifacts, the cross point of which indicates the location of a defective portion (d) in the tested sample.

In the measurement mode, when inspection sample 4 contains an inner defect d as shown in FIG. 3 and three projections are employed to complete the test of inspection sample 4, three artifacts a1 to a3 appear in the tomographic image displayed at CRT 15. Thus, when an X-ray path of one projection (e.g., the 1st projection) passes through the portion of defect d, the magnitude of X-ray absorption of this X-ray path differs from that of another X-ray path which does not pass through the defective portion. Then, the X-ray path passing through defect d provides the artifact a1 due to the X-ray absorption difference. Similarly, an X-ray path of the 2nd projection passing through defect d provides the artifact a2, and an X-ray path of the 3rd projection passing through defect d provides the artifact a3.

As seen from the illustration in FIG. 3, plural artifacts a1 to a3 cross at the position of defect d. Accordingly, if a function of the linear line of artifact a1 and that of artifact a2 (or a3) are measured by a suitable means, the geometrical location of defect d in the sample 4 can be known from a mathematical method (e.g., a computer calculation). If the width of two artifacts is measured, the size of defect d can be also known. A more simple method for measuring the geometrical location and/or the size of defect d is the use of a "scaled grating gate" provided in front of the screen of CRT display 15, as shown in FIG. 3.

Incidentally, if the tomographic image of inspection sample 4 is obtained from all of the projections (600 projections) without use of the tomographic image data of the reference sample, the artifacts indicating the location of the defect cannot be obtained in the displayed image. From this, a small number of projections is suitable for the test of inspection sample 4.

According to the configuration of FIG. 2A, since the size, dimensions, internal configurations, etc. of industrial products to be mass-produced are nominally prefixed, only a small number (e.g., three) of the projections is sufficient to complete the test for respective inspection samples. This is one of the important features obtained from the embodiment of the present invention.

Further, according to the configuration of FIG. 2A, the geometrical location and/or the size of defect d in the inspection sample can be easily seen from the displayed plural artifacts. This is another important feature obtained from the embodiment of the present invention.

The FIG. 2A embodiment may be modified such that a plurality of reference image memories (22) are used for storing plural different tomographic image slices of a reference sample. For instance, if 16 slices along the Z axis of a tomographic image on the X-Y plane should be inspected, 16 reference image memories 22-1 to 22-16 are used. These memories 22-1 to 22-16 store 16 different image slices, respectively. According to such a modified embodiment, any desired tomographic image selected from 16 slices of an inspection sample can be optionally and quickly obtained by a key manipulation of console 8.

Further, three sets of the CT scanners of FIG. 2A may be employed in a manner that the first CT scanner is used for the 1st projection (rotation angle for 0 degrees), the second CT scanner is used for the 201st projection (120 degrees) and the third CT scanner is used for the 401st projection (240 degrees), for example. These first to third CT scanners are arranged in series so that an inspection sample continuously and sequentially passes through these CT scanners. In this case, in a measurement mode for test or inspection, there is no need to rotate the source-detector configuration (2, 3 in FIG. 2A), thereby saving time consumption required for the measurement of numerous inspection samples.

In addition, radiation source 2 may utilize a radio isotope.

Figure 4:
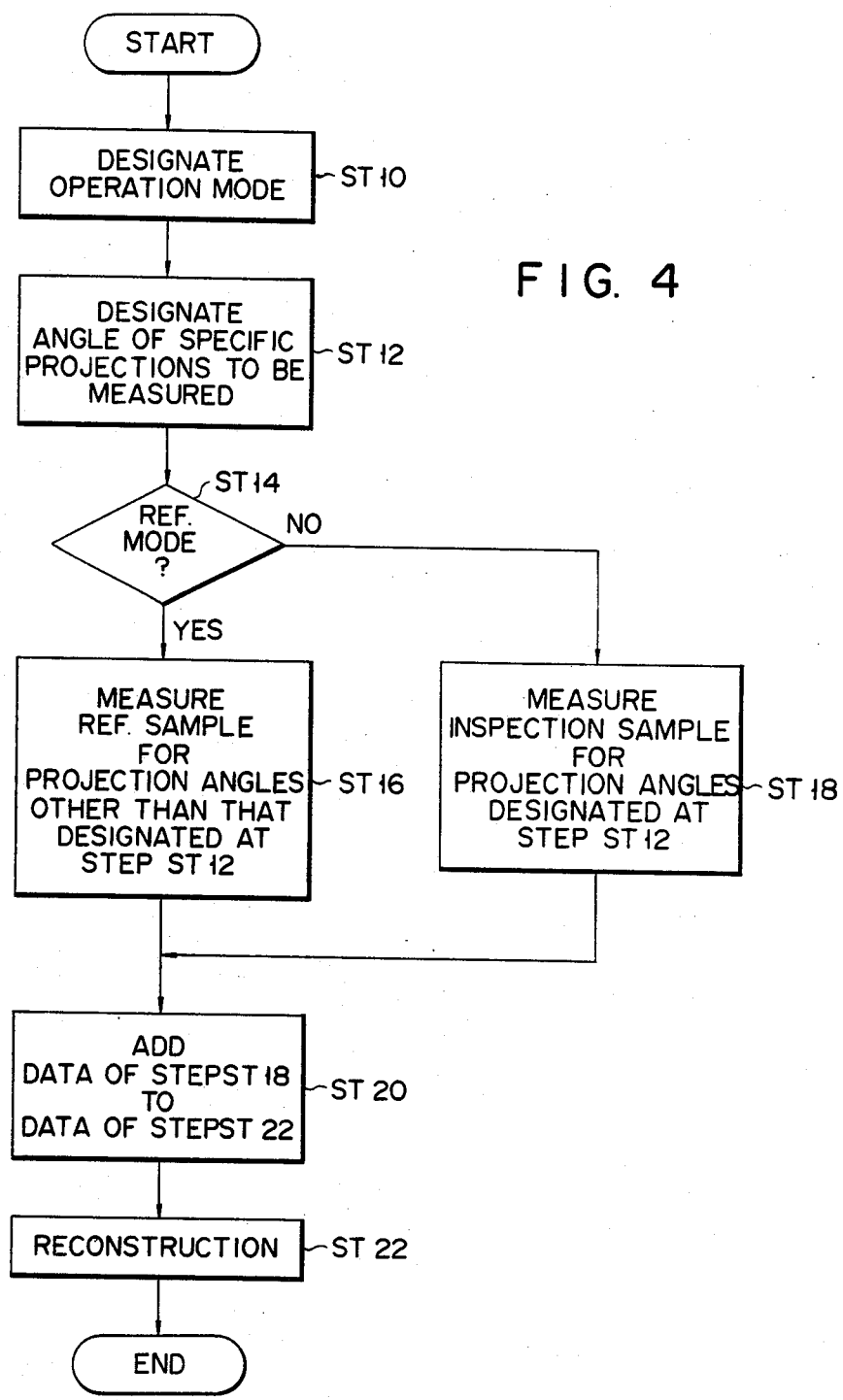
FIGS. 4 to 6 are flow charts respectively showing the control sequence of a system controller 7 in FIG. 2.

FIG. 4 is a flow chart showing a typical operational sequence of the CT scanner according to the present invention.

First, the mode of operation is designated by an operator of the CT scanner (ST 10). When an object material is a reference sample, the mode is designated as a reference data collection mode. When the object is an inspection sample to be tested, the mode is designated as a measurement mode. Next, the angles of specific projections for measuring or testing the inspection sample (e.g., 1st, 201st and 401st projections selected from 600 projections) are designated by the scanner operator (ST 12).

If the reference data collection mode is designated (YES at ST 14), the projection angles designated at step ST12 are omitted from measurement, and measurement for the reference sample with respect to the non-omitted projection angles is performed (ST16). If the measurement mode is designated (NO at ST14), measurement for the inspection sample with respect to the designated projection angles (1st, 201st and 401st projections) is performed (ST18). The projection data obtained at step ST18 is combined with or added to the projection data obtained at step ST16, so that projection data for a complete tomographic image is obtained (ST20). Then, the combined or added projection data is reconstructed (ST22).

Figure 5:
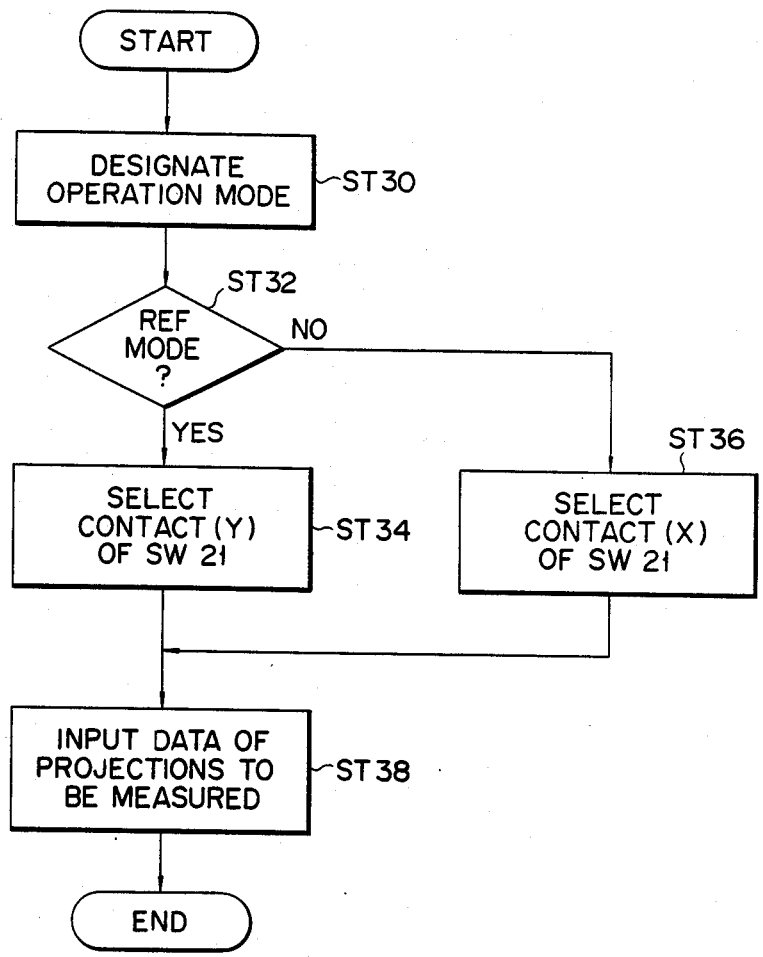

FIG. 5 is a flow chart showing a part of the control sequence effected by system controller 7 in FIG. 2A.

The mode of operation is designated by an operator of the CT scanner (ST 30). When a reference data collection mode is designated (YES at ST 32), controller 7 instructs the switch circuit 21 to select the contact Y (ST 34). When a measurement mode is designated (NO at ST 32), controller 7 instructs the switch circuit 21 to select the contact X (ST 36). After the contact selection of switch circuit 21, projection data is inputted to the configuration of elements 9 to 12 (ST38), so that measurement (collection of projection data, preprocessing, reconstruction, etc.) is effected.

Assume here that 600 projections are assigned to obtain a complete tomographic image of the object and that projection data in the reference data collection mode are obtained from 2nd-200th, 202nd-400th and 402nd-600th projections. Then, if switch circuit 21 selects the contact Y, reconstructed projection data of the referemce sample is stored at the 2nd-200th, 202nd-400th and 402nd-600th addresses of memory 22, for example. When switch circuit 21 selects the contact X and projection data in the measurement mode are obtained from 1st, 201st and 401st projections, reconstructed projection data of the inspection sample are stored at the 1st, 201st and 401st addresses of memory 13, for example.

Thereafter, the projection data (D21Y) stored at the 2nd-200th, 202nd-400th and 402nd-600th addresses of memory 22 and the projection data (D21X) stored at the 1st, 201st and 401st addresses of memory 13 are read out according to command I7 from system controller 7, and these data (D21Y, D21X) from memories 22 and 13 are added together in adder 220. In this addition, memories 13, 22 and adder 220 are controlled by system controller 7 such that respective pixels of the reference sample correspond to those of the inspection sample. The added data (D21Y+D21X) thus obtained becomes a complete tomographic image data DT.

Figure 2B:
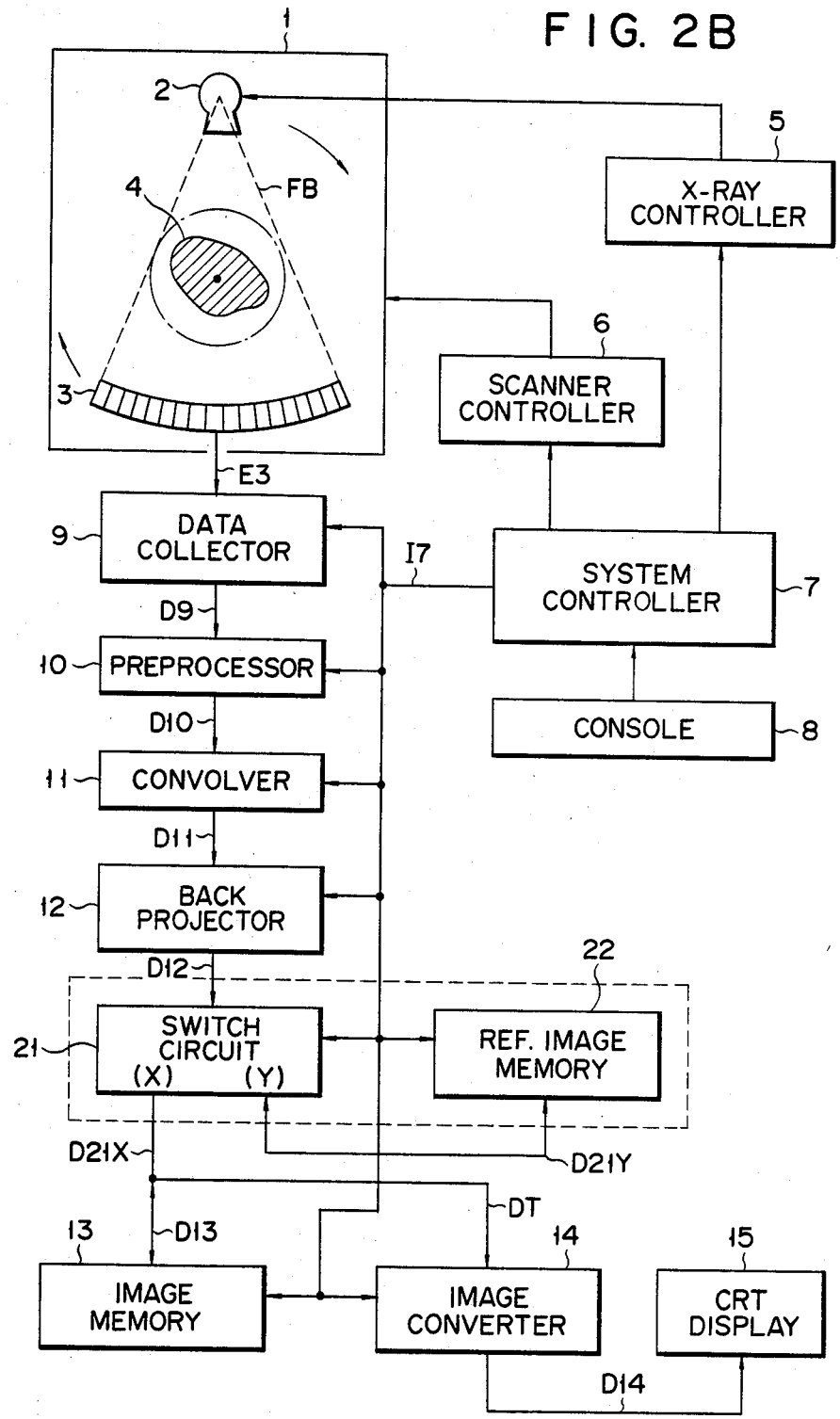
FIG. 2B shows a modification of the embodiment of FIG. 2A.

Or, according to a modification of the FIG. 2A apparatus as shown in FIG. 2B, the projection data (D21Y) of the reference sample stored at the 2nd-200th, 202nd-400th and 402nd-600th addresses of memory 22 are transferred via switch circuit 21 to memory 13. The transferred data are once stored at the 2nd-200th, 202nd-400th and 402nd-600th addresses of memory 13 in which the projection data (D21X) of the inspection sample are stored at 1st, 201st and 401st addresses. Then, the projection data (D21X+D21Y or D13) stored at the 1st-600th addresses are read out from memory 13 according to command I7. This read-out data (D13) corresponds to the complete tomographic image data DT.

Figure 6:
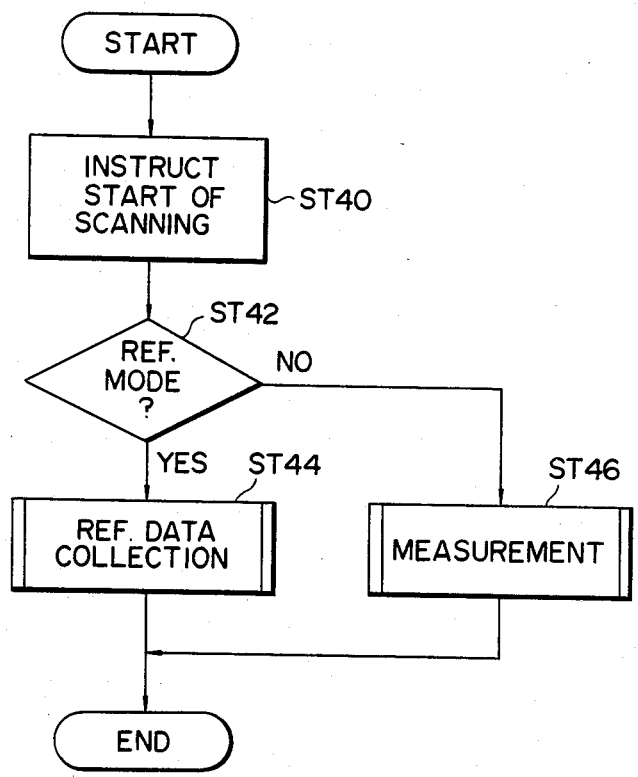

FIG. 6 is a general flow chart showing a basic operation of the CT scanner of the present invention. After the CT scanner operator starts the scanning (ST40), and if the mode is a reference data collection mode (YES at ST42), processing of the reference data collection is performed (ST44). If the mode is a measurement mode (NO at ST42), the measurement is carried out (ST46).

Figure 7:
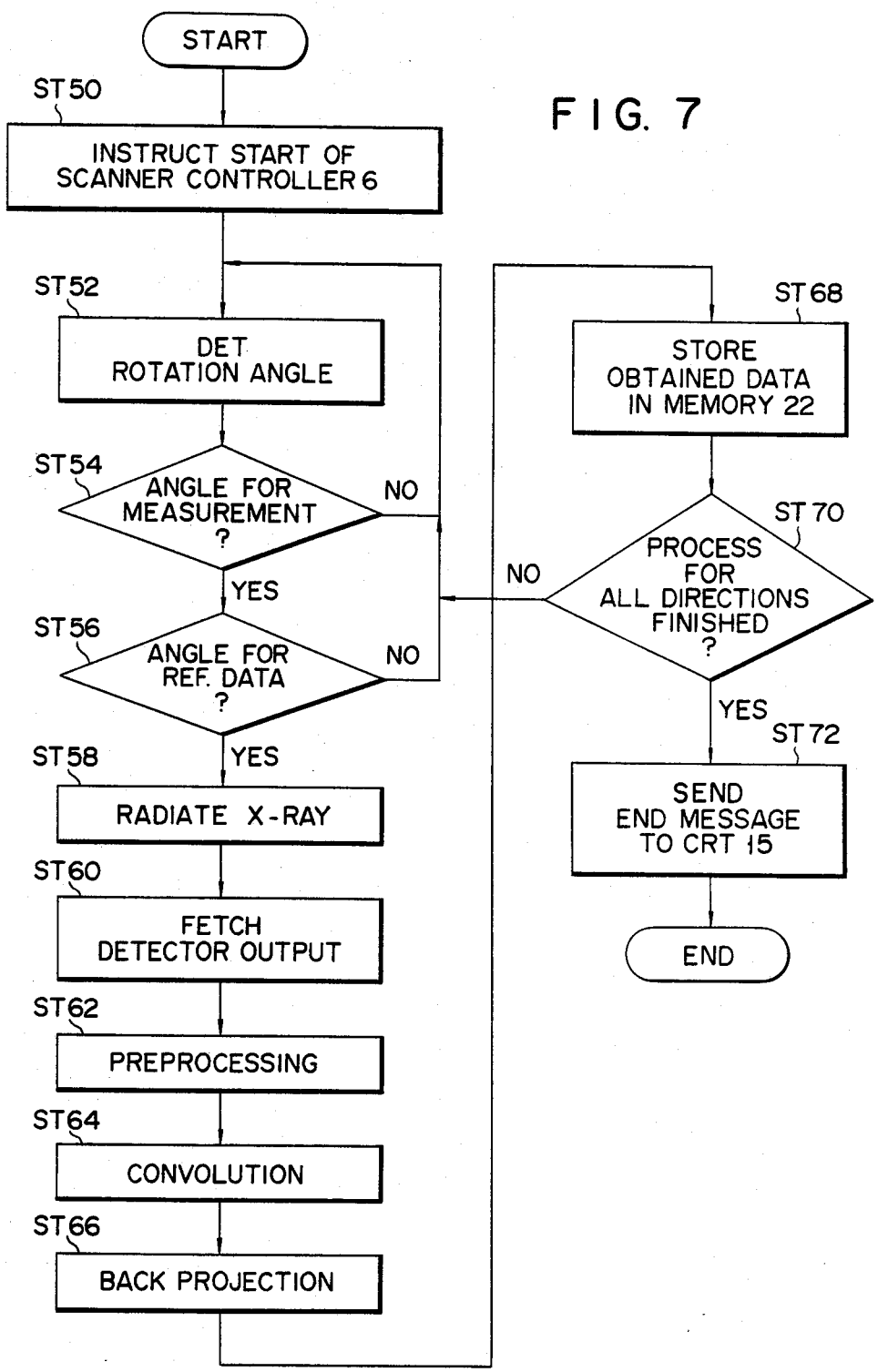
FIG. 7 is a flow chart showing details of step ST44 in FIG. 6.

FIG. 7 shows a subroutine of the reference data collection step ST44 in FIG. 6.

In FIG. 7, after the start of operation of the scanner controller 6 (ST50), system controller 7 detects the rotation angle of the source-detector configuration 2+3 in FIG. 2A (ST52). If the detected angle is not an angle for the measurement, e.g., if the detected angle does not correspond to any of given 1st to 600th projections (NO at ST54), the flow returns to step ST52, and the next rotation angle of the source-detector configuration is detected (ST52). When the detected angle corresponds to one of the given 1st to 600th projections (YES at ST54), whether or not the detected angle corresponds to one of the reference data collection mode is checked. If the detected angle does not correspond to one of the reference data collection mode (NO at ST56), e.g., if the detected angle does not correspond to any of the 2nd–200th, 202nd–400th and 402nd–600th projections, the flow returns to step ST52, and the next rotation angle of the source-detector configuration is detected (ST52). When the detected angle corresponds to one of the reference data collection mode (YES at ST56), e.g., when the detected angle corresponds to any of 2nd–200th, 202nd–400th and 402nd–600th projections, an X-ray with a given intensity is temporarily radiated (ST58). Then, digital data representing outputs E3 from the radiation detectors is fetched by system controller 7 (ST60).

After the data fetch is finished, the preprocessing, convolution and back projection for the fetched data are effected by elements 10 to 12 in FIG. 2A (ST62–ST66). Then, reconstructed image data is obtained. This obtained data is stored in memory 22 (ST68). If all the reconstructed image data for all of the projection angles (angles for 2nd–200th, 202nd–400th and 402nd–600th projections) in the reference data collection mode is not obtained (NO at ST70), the flow returns to step ST52. When all the reconstructed image data for all of the projection angles in the reference data collection mode is obtained (YES at ST70), an "END" message is displayed at CRT 15 in FIG. 2 (ST72) and the subroutine of FIG. 7 is finished.

Figure 8:
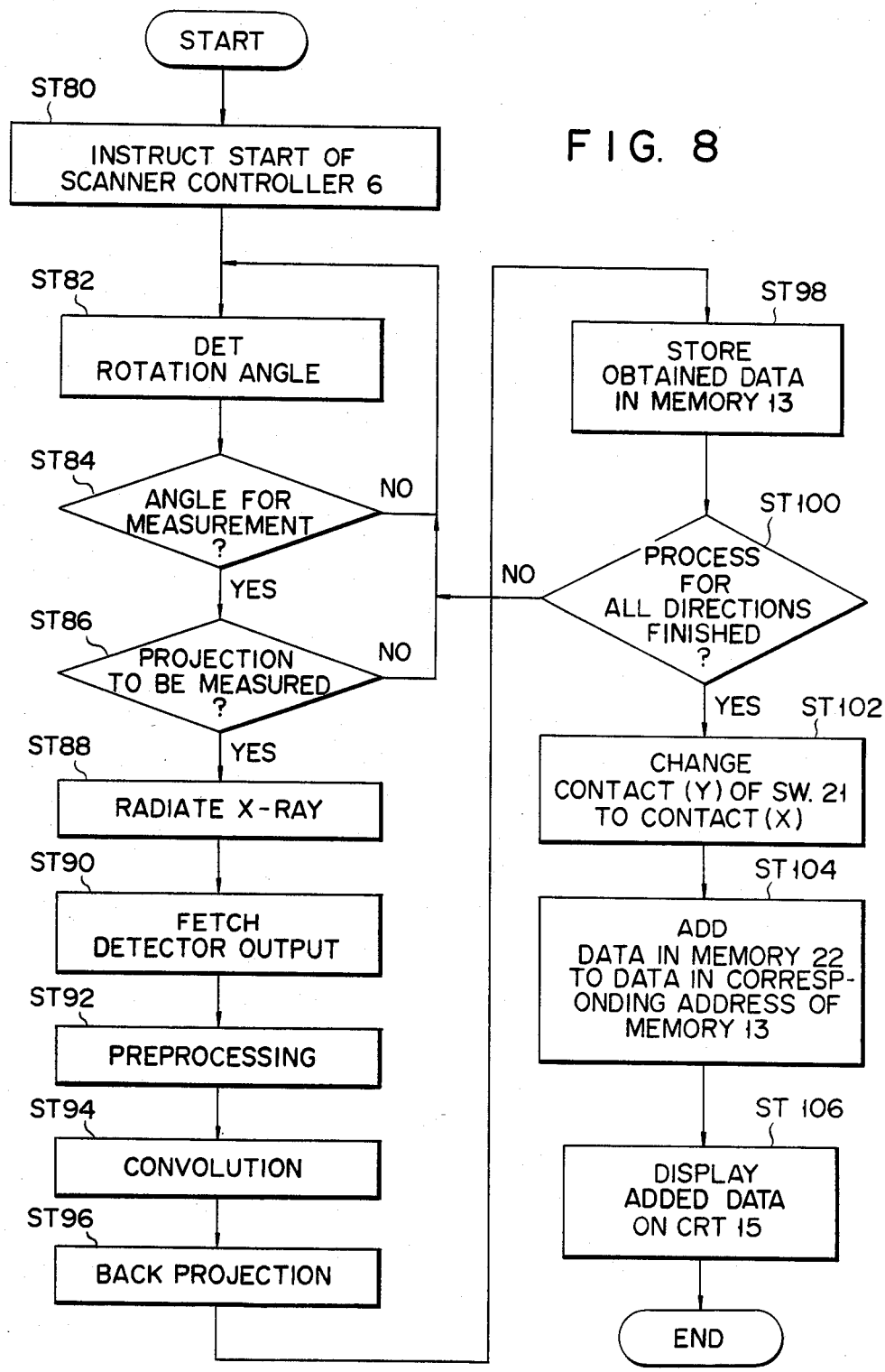
FIG. 8 is a flow chart showing details of step ST46 in FIG. 6.

FIG. 8 shows a subroutine of the measurement step ST46 in FIG. 6.

In FIG. 8, after the start of operation of scanner controller 6 (ST80), system controller 7 detects the rotation angle of the source-detector configuration 2+3 in FIG. 2A (ST82). If the detected angle is not an angle for the measurement, e.g., if the detected angle does not correspond to any of the given 1st to 600th projections (NO at ST84), the flow returns to step ST82, and the next rotation angle of the source-detector configuration is detected (ST82). When the detected angle corresponds to one of the given 1st to 600th projections (YES at ST84), whether or not the detected angle corresponds to one of the projections for the measurement mode is checked. If the detected angle does not correspond to one of the projections for the measurement mode (NO at ST86), e.g., if the detected angle does not correspond to 1st, 201st or 401st projection, the flow returns to step ST82, and the next rotation angle of the source-detector configuration is detected (ST82). When the detected angle corresponds to one of the projections for the measurement mode (YES at ST86), e.g., when the detected angle corresponds to 1st, 201st or 401st projection, an X-ray with a given intensity is temporarily radiated (ST88). Then, digital data representing outputs E3 from the radiation detectors is fetched by system controller 7 (ST90).

After the data fetch is finished, the preprocessing, convolution and back projection for the fetched data are effected by elements 10 to 12 in FIG. 2A (ST92–ST96). Then, reconstructed image data is obtained. This obtained data is stored in memory 13 (ST98). If all the reconstructed image data for all of the projection angles (angles for 1st, 201st and 401st projections) in the measurement mode is not obtained (NO at ST100), the flow returns to step ST82. When all the reconstructed image data for all of the projection angles in the measurement mode is obtained (YES at ST100), the selected contact (Y) of switch circuit 21 is changed to the contact (X) (ST102). Then, the contents of memory 22 (reference sample data) is added to the contents of memory 13 (inspection sample data) to obtain a complete tomographic image data (ST104). The obtained tomographic image data is displayed at CRT 15 (ST106) and the subroutine of FIG. 8 is finished.

Figure 9:
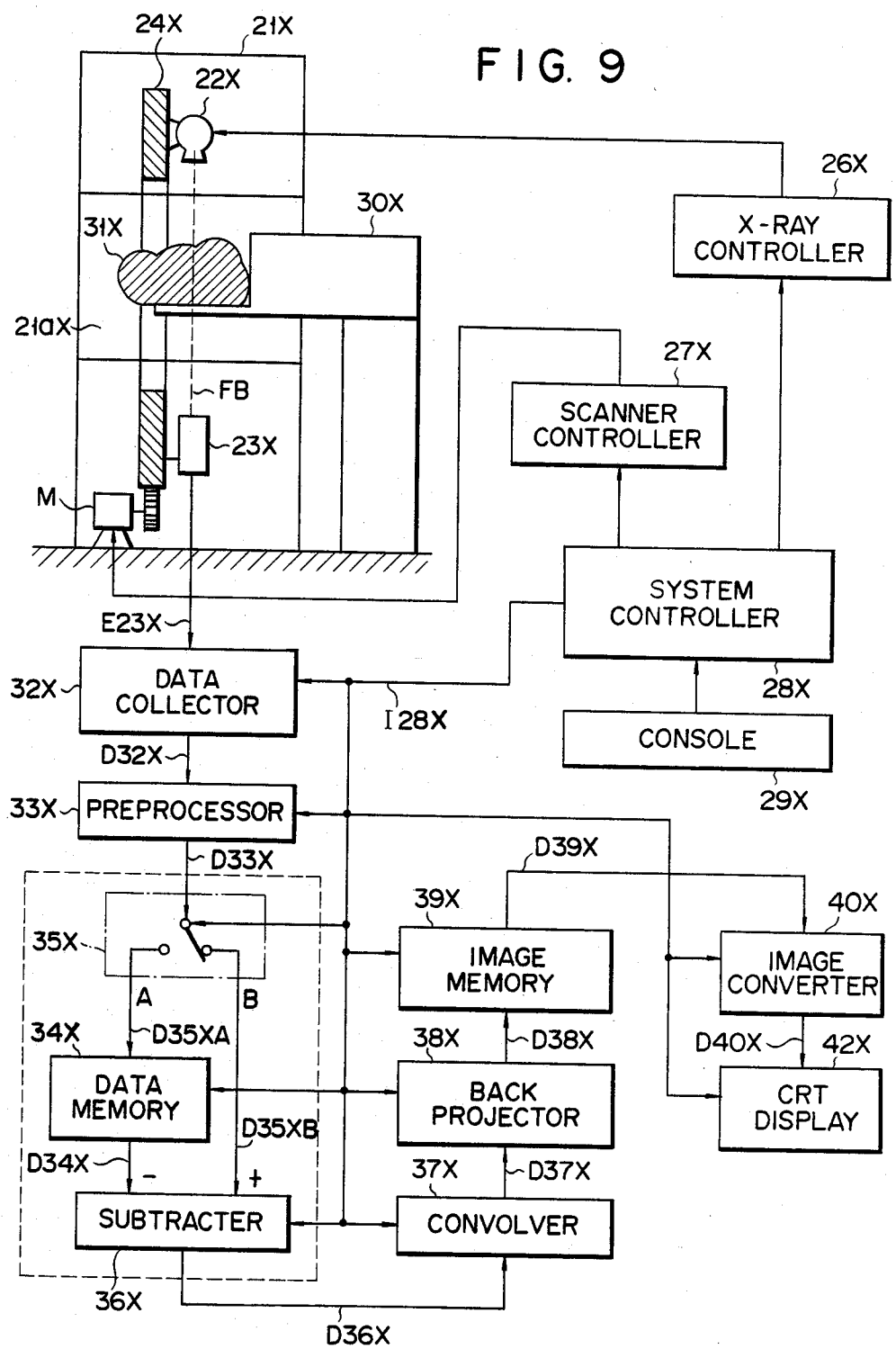
FIG. 9 shows a configuration of an X-ray tomographic testing apparatus according to another embodiment of the present invention.

FIG. 9 shows a configuration of an X-ray tomographic testing apparatus according to another embodiment of the present invention. In FIG. 9, the reference numeral 21X denotes a scanner main body (which corresponds to element 1 in FIG. 2A). The reference numeral 22X denotes an X-ray source (which corresponds to element 2 in FIG. 2A) for generating a fan beam X-ray having a given spreading width. The reference numeral 23X denotes a radiation detector (which corresponds to element 3 in FIG. 2A) being opposite X-ray source 22X. Radiation detector 23X is formed with a large number of tiny radiation sensors. The radiation sensors are arranged around the spreaded fan beam X-ray and serve to detect, with a certain spatial resolution, the intensity of X-rays from X-ray source 22X. X-ray source 22X and radiation detector 23X are mounted on a rotary actuator 24X in a manner that a tomography region 21aX is located at the center between source 22X and detector 23X. Rotary actuator 24X serves to effect a one-way step rotation of the sorce-detector configuration (22X+23X) with a given angle. The reference numeral 31X denotes an object material (sample to be tested) placed in tomography region 21aX. The reference numeral 30X denotes a support member. Support member 30X serves to hold the object material 31X at tomography region 21aX.

The reference numeral 26X denotes an X-ray controller (which corresponds to element 5 in FIG. 2A). Controller 26X controls the tube current and tube voltage of an X-ray tube in X-ray source 22X. The reference numeral 27X denotes a scanner controller (which corresponds to element 6 in FIG. 2A). Controller 27X allows to transmit the rotational power from a drive source M to rotary actuator 24X. The actuation of rotary actuator 24X is controlled by controller 27X. The reference numeral 28X denotes a system controller (which corresponds to element 7 in FIG. 2A). Controller 28X controls the whole operation of the tomographic testing apparatus. The reference numeral 29X denotes a console (which corresponds to element 8 in FIG. 2A). Console 29X is provided for inputting various instructions, data, etc. Console 29X is manipulated by a system operator when instructions and/or data, etc. are inputted to the testing apparatus.

The reference numeral 32X denotes a data collector (which corresponds to element 9 in FIG. 2A). Collector 32X receives respective outputs E23X from the radiation sensors in detector 23X. Data collector 32X delivers X-ray absorption data D32X corresponding to A/D converted radiation sensor outputs E23X. The reference numeral 33X denotes a preprocessor (which corresponds to element 10 in FIG. 2A). Preprocessor 33X receives X-ray absorption data D32X for each of the projections collected by data collector 32X. Preprocessor 33X performs prescribed preprocessing such as a gain correction, off-set correction, etc. and delivers preprocessed data D33X corresponding to the inputted X-ray absorption data D32X.

The reference numeral 34X denotes a data memory. Memory 34X stores preprocessed data D33X corresponding to X-ray absorption data D32X of respective projections collected in a reference data collection mode. The reference numeral 35X denotes a switch. Switch 35X is provided between preprocessor 33X and memory 34X and is used for switching the data transmission of D33X. According to a mode designation by console 29X, switch 35X is controlled by a command I28X from system controller 28, such that the contact A of switch 35X is selected in a reference data collection mode while the contact B thereof is selected in a measurement mode. Memory 34X is coupled to the contact A of switch 35X so that it may receive and store the data D35XA (D33X) from preprocessor 33X.

The reference numeral 36X denotes a subtracter. Subtracter 36X receives data D34X from memory 34X and data D35XB (D33X) from preprocessor 33X via the contact B of switch 35X. Subtracter 36X delivers data D36X representing a difference (D34X−D35XA) between the data D34X and the data D35XB obtained in the measurement mode. Here, it should be noted that subtracter 36X is controlled by system controller 28X, such that the projection of one subtraction input data coincides with the projection of the other subtraction input data, and that the X-ray path of one subtraction input data is identified with the X-ray path of the other subtraction input data.

The reference numeral 37X denotes a convolver (which corresponds to element 11 in FIG. 2A). Convolver 37X convolutes the preprocessed difference data D36X from subtracter 36X and outputs convoluted data D37X. The reference numeral 38X denotes a back projector (which corresponds to element 12 in FIG. 2A). Back projector 38X back-projects the convoluted data D37X along the projection direction and generates reconstructed image data D38X. The reference numeral 39X denotes an image memory (which corresponds to element 13 in FIG. 2A) for storing the reconstructed image data D38X. The stored contents of memory 39X can be optionally read out as data D39X in accordance with command I28X from system controller 28X. The reference numeral 40X denotes an image converter (which corresponds to element 14 in FIG. 2A). Converter 40X serves to convert a desired range of CT values of the data D39X (data with respect to levels of the X-ray absorption) into video data D40X having desired gradations or given colors. The reference numeral 42X denotes a CRT display (which corresponds to element 15 in FIG. 2A). CRT 42X displays the tomographic image of data D39X with given gradations and/or given colors.

In the above embodiment, although the subtraction (D35XB−D34X) is performed after the preprocessing, the subtraction may be performed after the convolution or after the back projection.

The operation of the testing apparatus in FIG. 9 is initiated by the manipulation of a system operator through console 29X.

The FIG. 9 embodiment employs two different modes, i.e., a reference data collection mode and a measurement mode. Each of these modes can be designated through console 29X. In the reference data collection mode, data of a reference reconstructed image (i.e., data of the reference sample) is collected. At this time, a standard model having no inner defect and no size/dimension errors is used for the reference sample, and a routine measuring operation for the reference sample is performed.

Thus, reference sample (object material) 31X is mounted on support 30X so that sample 31X is fixed within tomography region 21aX, and an instruction designating the reference data collection mode is given from console 29X. Then, system controller 28X allows the switch 35X to select the contact A. When a scanning start instruction (start instruction for tomograming) is delivered from console 29X, system controller 28X causes the scanner controller 27X to perform a rotation drive control for a given step rotation of rotation actuator 24X. At this time, system controller 28X also causes the X-ray controller 26X to supply, for each of the above step rotations, a given tube current and given tube voltage to X-ray source 22X by a prescribed period. Then, pulsate fan beam X-rays FB are sequentially radiated from source 22X. Since object material 31X is placed at the rotation center (tomography region) of actuator 24X and since detector 23X mounted on actuator 24X faces X-ray source 22X mounted thereon through the rotation center, X-ray source 22X is allowed to radiate the fan beam X-rays FB from various directions toward a given slice of material 31X. The radiation transmittance values of respective X-ray paths in the fan beam X-rays FB are sensed by radiation sensors in radiation detector 23X, and the sensed values are converted into electrical signals E23X.

The above converted signals E23X are collected by data collector 32X in which the collected signals are A/D converted into data D32X. In preprocessor 33X, A/D converted data D32X is subjected to a log conversion, gain correction, off-set correction and so on for each one projection. Preprocessed data D33X from preprocessor 33X (X-ray absorption data of respective X-ray paths for each projection) is supplied via the contact A of switch 35X to memory 34X. Memory 34X stores the supplied data (D35XA) for each projection. The above is the operation in the reference data collection mode.

When the measurement mode is designated through the manipulation of console 29X, object material (inspection sample) 31X to be tested is fixed at the given location of support 30X. Since a deviation between the set position of the reference sample and that of the inspection sample disturbs an accurate measurement, the testing apparatus is so arranged that a precise positioning of the object material is ensured. This may be achieved by providing a referencing plane used for the positioning. After the positioning of inspection sample 31X is completed, if an instruction designating the measurement mode is given from console 29X, system controller 28X causes the switch 35X to select the contact B. Under this condition, when a scanning start instruction is given, the measuring operation is performed, so that the prescribed projection data is collected, said preprocessing is effected, and the preprocessed projection data D35XB is supplied to subtracter 36X from the contact B of switch 35X.

On the other hand, projection data D34X whose projection is identified with the projection of the above preprocessed projection data D35XB is read out from memory 34X. Then, the read-out projection data D34X is supplied to subtracter 36X. In subtracter 36X, the projection data D34X (D35XA) obtained in the reference data collection mode is subtracted from the projection data D35XB obtained in the measurement mode. The subtracted data D36X from subtracter 36X is supplied to convolver 37X in which a convolution is effected. The convoluted data D37X is back-projected in back projecter 38X, and the back-projected data D38X is stored in memory 39X. Then, the reconstruction of a tomographic image is completed.

Figure 10:
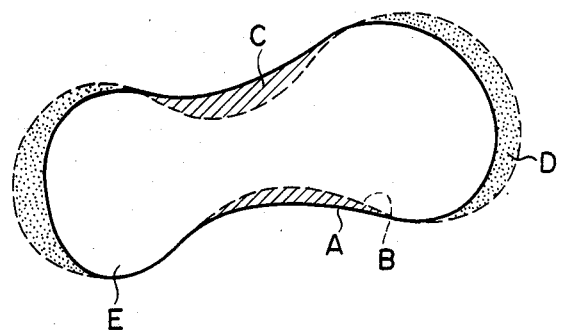
FIGS. 10 and 11 respectively illustrate tomographic image of the differece between a reference sample and a tested inspection sample.

An example of the reconstructed tomographic image is shown in FIG. 10. In FIG. 10, the solid line A indicates the outline of the reference sample, the broken line B indicates the outline of the inspection sample, the slant-lined area C indicates a minus area of CT values, the dotted area D indicates a plus area of CT values, and another area E indicates zero CT values.

Thus, in major pixel positions at which CT values are the same as the corresponding CT values of the reference sample, the subtraction of the inspection sample CT value from the reference sample CT value results in providing a zero CT value (area E). When the inspection sample has an extra portion while the reference sample does not have the corresponding portion, such an extra portion provides a plus CT value (area D). When the inspection sample has a lacking portion while the reference sample does not have the corresponding portion, such a lacking portion provides a minus CT value (area C). From this, if the CT value minus portion (C), the CT value zero portion (E) and the CT value plus portion (D) are colored by "red", "blue" and "yellow", respectively, and such a colored difference image of the reconstructed tomographic image is displayed at color CRT display 42X, the lacking and extra portions of the inspection sample are impressively known to the system operator. Of course, these lacking and extra portions may be discriminated from one another by assigning specific gradations.

According to the abovementioned embodiment, since the different portions of the inspection sample with respect to the reference sample are clearly known from the displayed image, an accurate inspection of defect, size and/or dimensions of the tested material is ensured. The above embodiment is suitable to inspect a predetermined slice of a sample being formed of a uniform material.

Although the above description is given in a case wherein a sample of unifom material is measured, it is possible to display the difference between a reference sample and a non-uniform material sample by means of various concentrations of the image density.

Figure 11:
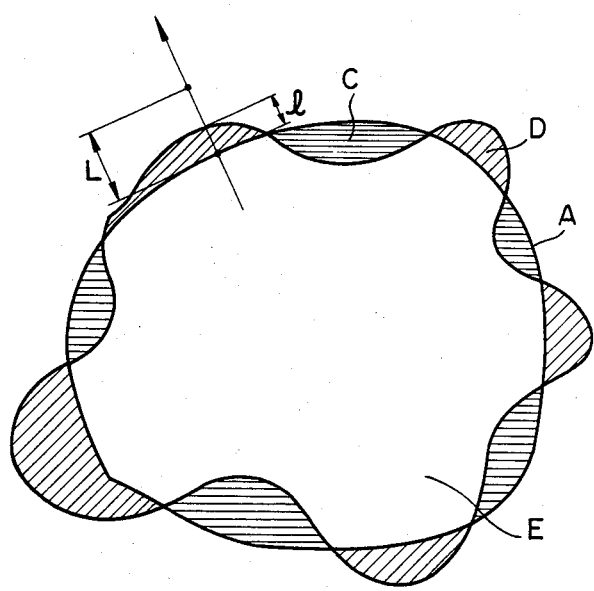

Further, as shown in FIG. 11, the difference between a reference sample and an inspection sample may be exaggeratedly displayed. In the illustration of FIG. 11, the amount (length) of the difference is expanded. An exaggerated image can be obtained by modifying a non-exaggerated image in such a manner that the length of the difference along the normal direction of the outline of the reference sample is elongated. Although such difference expansion deforms the image of the actual figure of an inspection sample, since the character of the difference is exaggerated, such an exaggerated display is impressive and suitable for a visual monitor.

Figure 12:
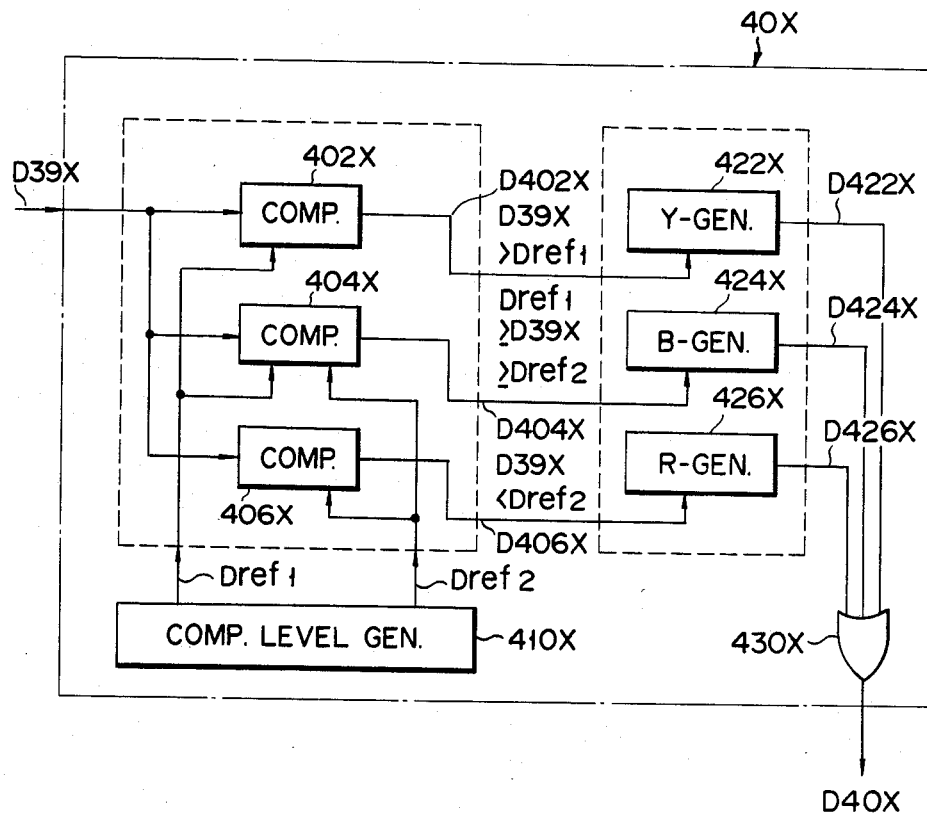
FIG. 12 shows details of a color converter 40X in FIG. 9.
Figure 13:
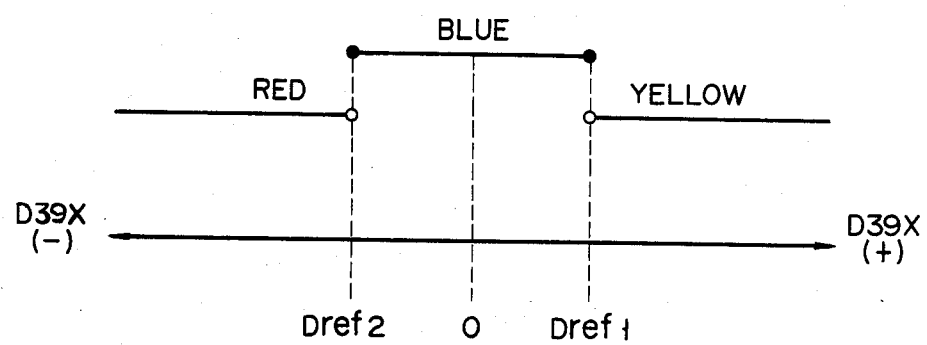
FIG. 13 is a graph explaining the operation of the color converter in FIG. 12.

FIG. 12 shows details of a color converter 40X in FIG. 9. FIG. 13 is a graph explaining the operation of color converter 40X. (Image converter 14 in FIG. 2A or 2B may have the FIG. 12 configuration, of course.) In FIG. 12, data D39X from memory 39X is inputted to three digital comparators 402X, 404X and 406X. Each of comparators 402X and 404X receives first referece level data Dref1, and each of comparators 404X and 406X receives second referece level data Dref2. Reference level data Dref1 and Dref2 are obtained from a comparison level generator 410X.

Comparator 402X generates a comparison result output D402X when D39X>Dref1. This output D402X is supplied to a color generator 422X for generating "yellow" data D422X (D39X>Dref1 in FIG. 13). Comparator 404X generates a comparison result output D404X when Dref1≧D39X≧Dref2. This output D404X is supplied to a color generator 424X for generating "blue" data D424X (Dref1≧D39X≧Dref2 in FIG. 13). Comparator 406X generates a comparison result output D406X when D39X<Dref2. This output D406X is supplied to a color generator 426X for generating "red" data D426X (D39X<Dref2 in FIG. 13). Data D422X, D424X and D426X are inputted to an OR gate 430X and the ORed output therefrom is supplied as the data D40X to color CRT display 42X.

FIG. 14 shows a distribution of binary-coded "1" data around the boundary (line A in FIG. 11) of a reference sample. FIGS. 15A to 15J illustrate how the pattern classification of binary-coded "1" data around the boundary of an inspection sample is effected. (In FIGS. 14 and 15, the black and white tiny circles denote pixels of binary "1" data.) FIG. 16 is a flow chart explaining how emphasizing or exaggerating the difference between a reference sample and a tested inspection sample is achieved.

After the start of the operation of FIG. 9 apparatus, all binary-coded "1" data at the boundary region of a reference sample (black circles in FIG. 14) is extracted from the data in memory 34X (ST110 in FIG. 16). Then, each presently obtained binary-coded "1" data of inspection sample 31X is classified to obtain binary-coded "1" data at the boundary region of inspection sample 31X (ST112). After obtaining binary-coded "1" data at the boundary region of inspection sample 31X and also obtaining binary-coded "1" data at the corresponding boundary region of the reference sample, along each of the prescribed directions as exemplified by arrows in FIGS. 15A to 15J, a length l (FIG. 11) between the corresponding pixels of the reference and inspection samples is calculated (ST114). The calculated length l is multiplied by a given coefficient α so that the length l is elongated to L ($=\alpha \times l$) (ST116).

The above process for obtaining the elongated length data L is repeated until this processing is completely effected on all binary-coded "1" data at the boundary region of inspection sample 31X. If the processing is not completed, the process for obtaining the data L is sequentially applied to the next unprocessed boundary data at the boundary region of inspection sample 31X (NO at ST118 and ST120). When the above processing is completed, the difference exaggerating operation is finished (YES at ST118). The data L thus obtained is used for displaying the exaggerated tomographic image.

Figure 17:
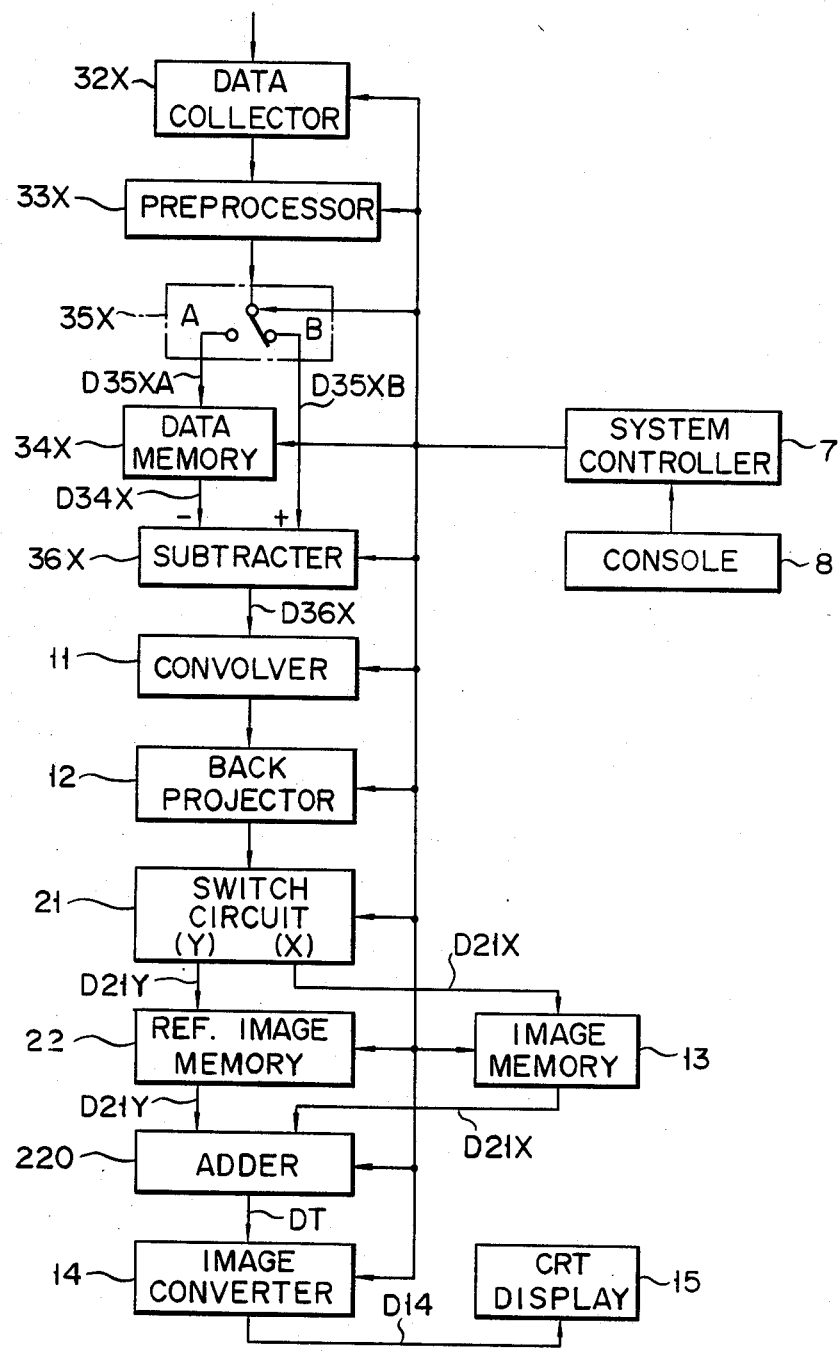
FIG. 17 shows a configuration of an X-ray tomographic testing apparatus according to another embodiment of the present invention, which corresponds to the combination of the embodiments of FIGS. 2A and 9.

FIG. 17 shows a configuration of an X-ray tomographic testing apparatus according to another embodiment of the present invention. This embodiment corresponds to the combination of FIGS. 2A and 9. According to this embodiment, the tomographic image (indicating defective portions only and containing artifacts) of an inspection sample is obtained from a small number (e.g., three) of the data collection, thereby achieving a speedy test.

The apparatus of FIG. 17 will operate as follows.

In a first step, raw data (D35XA) of a reference sample for all projections (e.g., 600 projections) are collected, preprocessed and stored in memory 34X.

In a second step, raw data (D35XB) of the reference sample for prescribed projections (e.g., 2nd-200th, 202nd-400th and 402nd-600th projections) are collected and preprocessed. Then, data (D36X) representing the difference between the first step preprocessed data (D34X=D35XA) stored in memory 34X and the second step preprocessed data (D35XB) is produced from subtracter 36X for each of the mutually-related projections, i.e., the difference between the first step data of an N projection and the second step data of the N projection is detected. (N projection is one of the 2nd–200th, 202nd–400th and 402nd–600th projections). The detected difference data (D36X) is reconstructed for said mutually-related projections (2nd–200th, 202nd–400th, 402nd–600th), and the reconstructed difference data (D21Y) is stored in reference image memory 22.

In a third step, projection data of an inspection sample for the 1st, 201st and 401st projections are collected and preprocessed. Then, the difference (D36X) between the first step preprocessed data (D34X) stored in memory 34X and the third step preprocessed data (D35XB) is detected for each of the mutually-related projections, i.e., the difference between the first step data of an M projection and the third step data of the M projection is detected. (M projection is one of the 1st, 201st and 401st projections). The detected difference data (D36X) is reconstructed for each of the mutually-related projections (1st, 201st, 401st), and the reconstructed difference data (D21X) is stored in image memory 13.

In a fourth step, the difference data (D21X) stored in memory 13 (1st, 201st and 401st projections) is added by adder 220 to the difference data (D21Y) stored in memory 22 (2nd–200th, 202nd–400th and 402nd–600th projections). Then, a reconstructed tomographic image data DT (for 600 projections) of the difference between the reference sample and the inspection sample is obtained from adder 220.

The FIG. 17 embodiment has the advantages of both of the embodiments of FIGS. 2A and 9.

Figure 18:
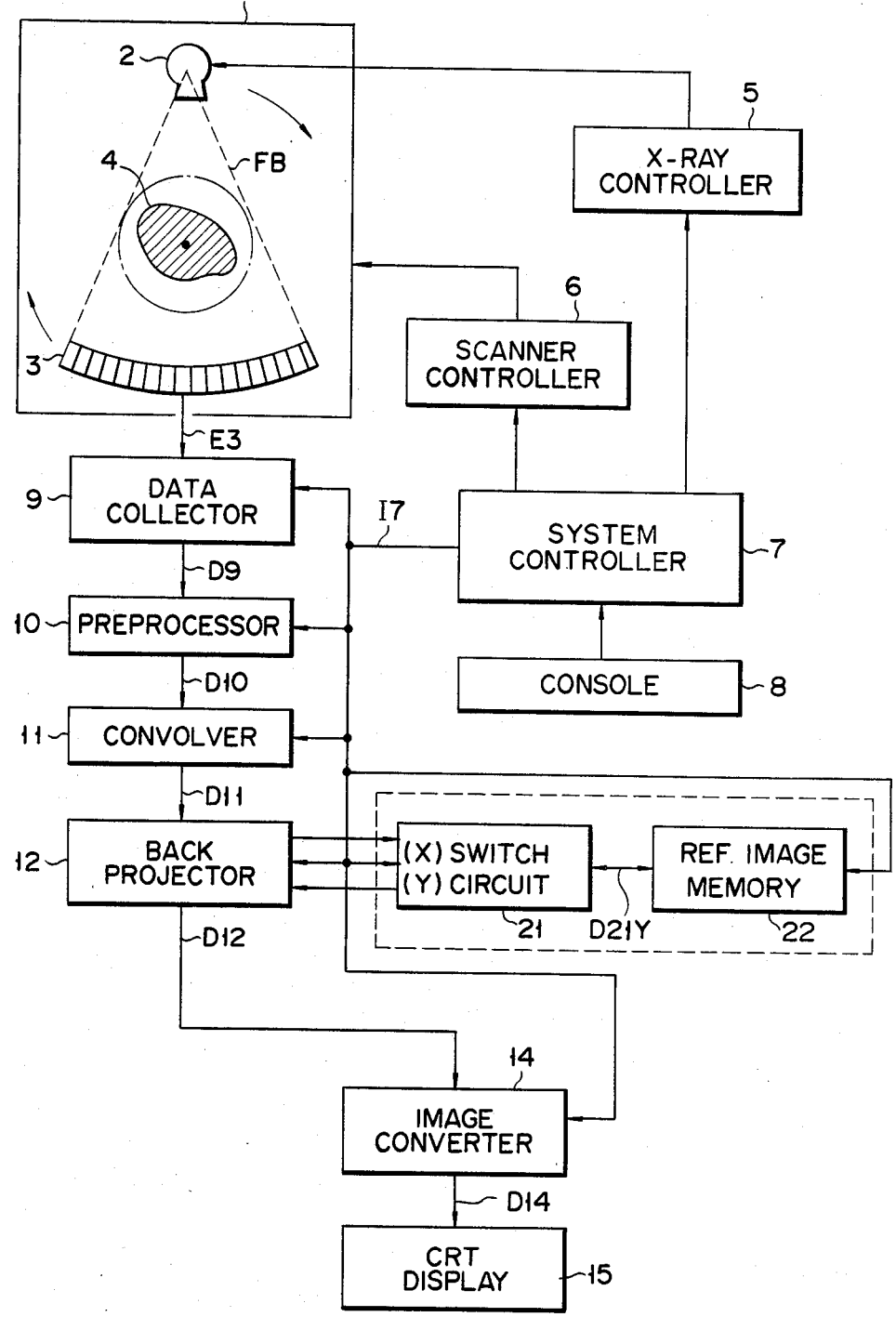
FIG. 18 shows another modification of the FIG. 2A embodiment.

FIG. 18 shows another modification of FIG. 2A embodiment. According to the FIG. 18 emdodiment, in the reference data collection mode, back-projected reference image data from back projector 12 is transferred via a signal port X of switch circuit 21 to reference image memory 22, and the transferred data is stored in memory 22. In the measurement mode, prior to perform the measuring of the inspection sample for each of the selected projections (e.g., 1st, 201st and 401st projections in 600 projections), the back-projected reference image data stored in memory 22 is set in back projector 12 via a signal port Y of switch circuit 21. Then, convoluted data D11 of an inspection sample from convolver 11 is back-projected and superposed upon the back-projected reference image data set in back projector 12, so that a reconstructed tomographic image data D12 (=DT) is obtained and transferred to image converter 14.

According to the configuration of FIG. 18, since the back projection for an inspection sample can be effected sequentially on the back-projected reference image data which is set in the back projector for each projection, the measuring speed for the inspection sample can be effectively enhanced and, in addition, the circuit configuration of the testing apparatus becomes simple.

Figure 19:
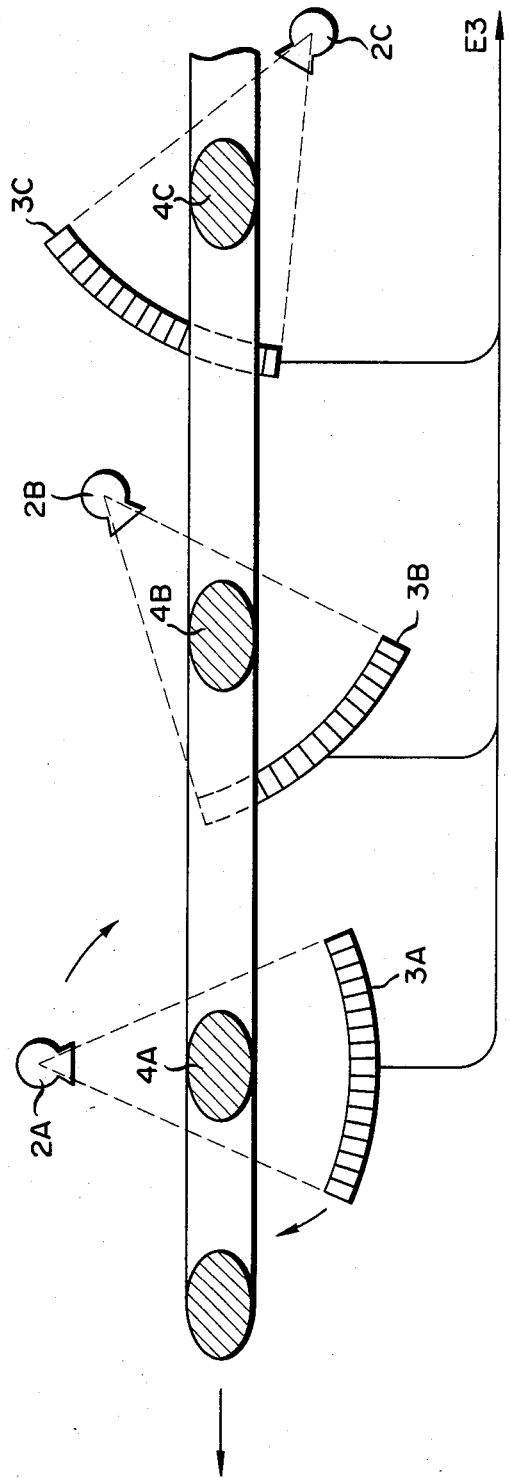
FIG. 19 shows a practical application of FIG. 2A, 2B, 9, 17 or 18 apparatus.

FIG. 19 shows a practical application of the apparatus of FIG. 2A, 2B, 9, 17 or 18. In the embodiment of FIG. 19, three sets of source-detector configurations 2A+3A, 2B+3B and 2C+3C are employed. The first set of source-detector configuration 2A+3A is rotatable around its tomography region through which object materials 4A, 4B, 4C, etc. are passed. The first set is used for collecting the reference sample data as well as collecting the inspection sample data of the 1st projection in given 600 projections. The second and third sets 2B+3B and 2C+3C are fixed with respect to their tomography regions. The second set is used for collecting the inspection sample data of 101st projection, and the third set is used for collecting the inspection sample data of 201st projection. If the projection angle of the first set 2A+3A is defined as 0 degrees, the projection angle of the second set 2B+3B with respect to the first set is 60 degrees and the projection angle of the third set 2C+3C is 120 degrees, as shown in FIG. 19.

According to the configuration of FIG. 19, in the measurement mode, the first set 2A+3A is fixed at 0 degrees. An inspection sample to be measured is transferred from the right hand side to the left hand side in the figure. When inspection sample 4C comes to the tomography region of the third set 2C+3C, only the third set performs the data collection for the 201st projection of a given slice of the sample. When the same sample 4B (=4C) comes to the tomography region of the second set 2B+3B, only the second set performs the data collection for the 101st projection of the same slice. When the same sample 4A (=4B) comes to the tomography region of the first set 2A+3A, only the first set performs the data collection for the 1st projection of the same slice. Then, the projection data of the inspection sample slice for the three projections is obtained. The operation timing for the data collection of the first to third source-detector sets is governed by the system controller 7 (or 28X).

The FIG. 19 arrangement is suitable when the testing apparatus is applied to a continuous inspection of mass-produced products on a belt conveyer.

The present invention should not be limited to the embodiment as mentioned above and illustrated in the figures. It is possible to optionally modify the embodiment without departing from the scope of the invention. For instance, although an X-ray is used in the above embodiment, another radiation such as a γ-ray, neutron or other like radiations may be similarly used in place of an X-ray.

Futher, although so-called "third generation CT equipment" (which employs a rotationally scanned fan beam for obtaining a tomographic image) is utilized in the explanation of the embodiment, the present invention may be applied to a first generation CT equipment in which a pencil beam is traversingly and rotatingly scanned to obtain a tomographic image, or applied to a second generation CT equipment in which a narrow width fan beam is traversingly and rotatingly scanned to obtain a tomographic image, or applied to a fourth generation CT equipment in which an object material to be inspected is surrounded by sensor elements and only a radiation source for radiating a fan beam is rotated at the time of scanning.

The following U.S. patents relates to the technical field of the invention. All disclosures of these U.S. patents are incorporated in the present application for the purpose of assisting the disclosure of the present invention.

(1) U.S. Pat. No. 4,075,492 issued on Feb. 21, 1978 (Boyd et al.)

(2) U.S. Pat. No. 4,138,721 issued on Feb. 6, 1979 (Boyd)

(3) U.S. Pat. No. 4,149,247 issued on Apr. 10, 1979 (Pavkovich et al.)

(4) U.S. Pat. No. 4,280,178 issued on July 21, 1981 (Nassi et al.)

(5) U.S. Pat. No. 4,293,912 issued on Oct. 6, 1981 (Walters)

What is claimed is:

1. A tomographic apparatus for testing an object material which is either a reference sample or an inspection sample, comprising:
   scanner means for generating and scanning a radiation beam within a given plane in which said object material is located, and providing a scanner output containing radiation absorption information of a given slice of said object material;
   reconstruction means, coupled to said scanner means, for reconstructing a tomographic image from said scanner output to provide reference image data and inspection image data, for storing said reference image data, and for providing tomographic image data corresponding to the stored reference image data and said inspection image data wherein said reference image data lacks information corresponding to said inspection image data, said inspection image data lacks information corresponding to said reference image data, and said tomographic image data corresponds to the combination of said reference image data and said inspection image data; and
   a display means coupled to said reconstruction means for displaying a tomographic image of said inspection sample in accordance with said tomographic image data.

2. A tomographic apparatus according to claim 1, wherein said reconstruction means includes:
   memory means for storing said inspection image data.

3. A tomographic apparatus according to claim 1, wherein said reconstruction means includes:
   reference memory means for storing reconstructed reference image data representing said reference sample; and
   back projector means responsive to the reconstructed reference image data from said reference memory means and to the scanner output containing information of said inspection sample, for reconstructing said inspection image data from the scanner output information, and providing said tomographic image data in accordance with the reconstructed reference image data and the reconstructed inspection image data.

4. A tomographic apparatus according to claim 1, wherein said reconstruction means reconstructs said scanner output to provide said reference image data which corresponds to a reconstructed image of said reference sample if said object material is said reference sample, and reconstructs said scanner output to provide said inspection image data which corresponds to a reconstructed image of said inspection sample if said object material is said inspection sample.

5. A tomographic apparatus according to claim 1, wherein said reconstruction means includes:
   reference image memory means for storing said reference image data when said object material is said reference sample;
   inspection image memory means for storing said inspection image data when said object material is said inspection sample; and
   means for combining said reference image data with said inspection image data to provide said tomographic image data.

6. A tomographic apparatus according to claim 1, wherein said display means includes:
   image converter means for modifying the gradation of said tomographic image data.

7. A tomographic apparatus according to claim 1, wherein said reconstruction means includes:
   difference means for providing boundary data corresponding to the difference between said reference image data and said inspection image data, said boundary data representing the difference between a boundary region of said inspection sample and that of said reference sample.

8. A tomographic apparatus according to claim 7, wherein said display means includes:
   image converter means for modifying said boundary data so that a tomographic image displayed at said display means exaggeratedly exhibits the portion of said difference between said reference image data and said inspection image data.

9. A tomographic apparatus according to claim 1, wherein said reconstruction means includes:
   difference means for providing boundary data corresponding to the difference between said reference image data and said inspection image data, said boundary data representing the difference between a boundary region of said inspection sample and that of said reference sample;
   reference image memory means for storing said reference image data when said object material is said reference sample;
   inspection image memory means for storing said inspection image data when said object material is said inspection sample;
   means for combining said reference image data with said inspection image data to provide said tomographic image data.

10. A tomographic apparatus according to claim 13, wherein said display means includes:
    image converter means for modifying said boundary data so that a tomographic image displayed at said display means exaggeratedly exhibits the portion of said difference between said reference image data and said inspection image data.

11. A tomographic apparatus according to claim 1, wherein said scanner means includes:
    system controller means, being responsive to a predetermined sequence, for obtaining said reference image data which lacks the information of said inspection image data, obtaining said inspection image data which lacks the information of said reference image data, and obtaining the reconstructed tomographic image data which corresponds to the sum of said reference image data and said inspection image data.

12. A tomographic apparatus according to claim 12, wherein said scanner means includes:
    system controller means, being responsive to a predetermined sequence, for effecting the modifying function of said image converter means, so that the amount of said difference is expanded.

13. A tomographic apparatus for testing an object material which is either a reference sample or an inspection sample, comprising:
    scanner means for generating and scanning a radiation beam within a given plane in which said object material is located, and providing a scanner output containing radiation absorption information of a given slice of said object material;
    reconstruction means, coupled to said scanner means, for reconstructing a tomographic image from said scanner output to provide reference image data and inspection image data, for storing said reference image data, and for providing tomographic image data corresponding to the stored reference image data and said inspection image data; and a display means coupled to said reconstruction means for displaying a tomographic image of said inspection sample in accordance with said tomographic image data wherein an image displayed at said display means contains a plurality of different artifacts each of which provides a portion of an image of a defect in said inspection sample, said defect image representing the difference between said reference sample and said inspection sample.

14. A tomographic apparatus according to claim 13, further comprising:

means for measuring the position of said defect at the cross-point of said plural artifacts.

15. A tomographic apparatus according to claim 13, further comprising:

means for measuring the size of said defect at the cross-point of said plural artifacts.

16. A tomographic testing method, comprising the steps of:

obtaining, by means of a CT scanning, a first given number of reference image data of a reference sample having no defect;

obtaining, by means of the CT scanning, a second given number of inspection image data of an inspection sample having defective portions, said second given number being smaller than first given number;

combining said inspection image data which lacks information corresponding to said reference image data, with said reference image data from which soecific data corresponding to said inspection image data is deleted, and providing tomographic image data representing said inspection sample; and displaying a tomographic image of said inspection data in accordance with said tomographic image data.

17. A tomographic testing method comprising the steps of:

obtaining, by means of a CT scanning, a first given number of reference image data of a reference sample having no defect;

obtaining, by means of the CT scanning, a second given number of inspection image data of an inspection sample having defective portions, said second given number being smaller than said first given number; combining said inspection image data with said reference image data from which specific data corresponding to said inspection image data is deleted, and providing tomographic image data representing said inspection sample;

displaying a tomographic image of said inspection sample in accordance with said tomographic image data;

detecting a plurality of different artifacts each of which passes a portion of defect in said inspection sample; and measuring one of the position and size of said defect in accordance with the cross-point of said plural artifacts.

* * * * *